(12) United States Patent
Medeiros

(10) Patent No.: US 9,028,460 B2
(45) Date of Patent: May 12, 2015

(54) HOLDER

(76) Inventor: Lester William Medeiros, Honolulu, HI (US)

( * ) Notice: Subject to any disclaimer, the term of this patent is extended or adjusted under 35 U.S.C. 154(b) by 426 days.

(21) Appl. No.: 12/386,551

(22) Filed: Apr. 18, 2009

(65) Prior Publication Data

US 2009/0270822 A1     Oct. 29, 2009

Related U.S. Application Data

(60) Provisional application No. 61/125,251, filed on Apr. 23, 2008.

(51) Int. Cl.
*A61F 5/453* (2006.01)
*A61F 5/455* (2006.01)
*A61F 5/457* (2006.01)
*A61F 5/451* (2006.01)

(52) U.S. Cl.
CPC ................ *A61F 5/453* (2013.01); *A61F 5/451* (2013.01)

(58) Field of Classification Search
USPC ............................ 604/346, 347, 349; 600/574
See application file for complete search history.

(56) References Cited

U.S. PATENT DOCUMENTS

| | | | | |
|---|---|---|---|---|
| 2,484,356 A * | 10/1949 | Ribeiro et al. | ................ | 604/347 |
| 2,529,999 A * | 11/1950 | Chambers | ................... | 604/347 |
| 4,886,508 A * | 12/1989 | Washington | .................. | 604/327 |
| 4,936,838 A * | 6/1990 | Cross et al. | ................... | 604/329 |
| 5,346,483 A * | 9/1994 | Thaxton, Sr. | ................. | 604/353 |
| 5,618,279 A * | 4/1997 | Pudlo | ....................... | 604/385.09 |
| 6,551,293 B1* | 4/2003 | Mitchell | ....................... | 604/353 |
| 6,635,038 B2* | 10/2003 | Scovel | .......................... | 604/353 |
| 7,143,768 B2* | 12/2006 | Miskie | ......................... | 128/885 |
| 7,815,619 B2* | 10/2010 | Miskie | ........................... | 604/349 |
| 7,875,010 B2* | 1/2011 | Frazier et al. | ................. | 604/329 |
| 2007/0073252 A1* | 3/2007 | Forgrave | ....................... | 604/349 |
| 2007/0185465 A1* | 8/2007 | Campbell et al. | ............. | 604/347 |
| 2010/0234820 A1* | 9/2010 | Tsai et al. | ...................... | 604/319 |
| 2011/0152802 A1* | 6/2011 | DiCamillo et al. | ........... | 604/349 |

* cited by examiner

*Primary Examiner* — Susan Su

(57) ABSTRACT

The present invention is a solution for continence problems. A supporting structure can be in the form of a modified jock strap or biker's shorts. It includes a male version and a unisex version. The male version comprises a urine-collecting bag having a top opening to receive the genitalia of the user, whereas the unisex version comprises a breathable pad configured to be positioned in a crotch area of the user. Both versions utilize micro channels for guiding urine away from the user.

8 Claims, 8 Drawing Sheets

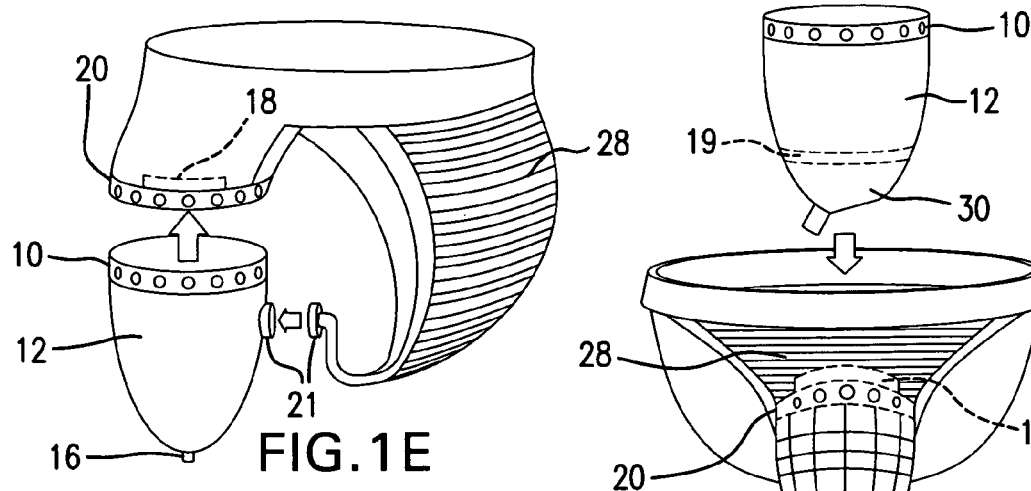
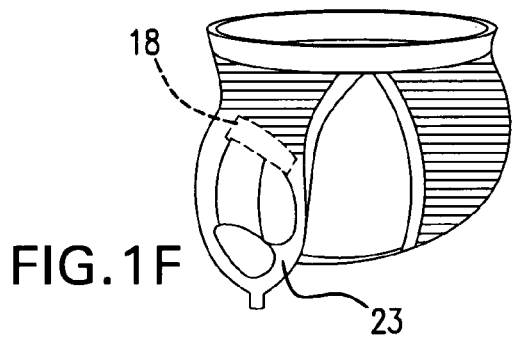
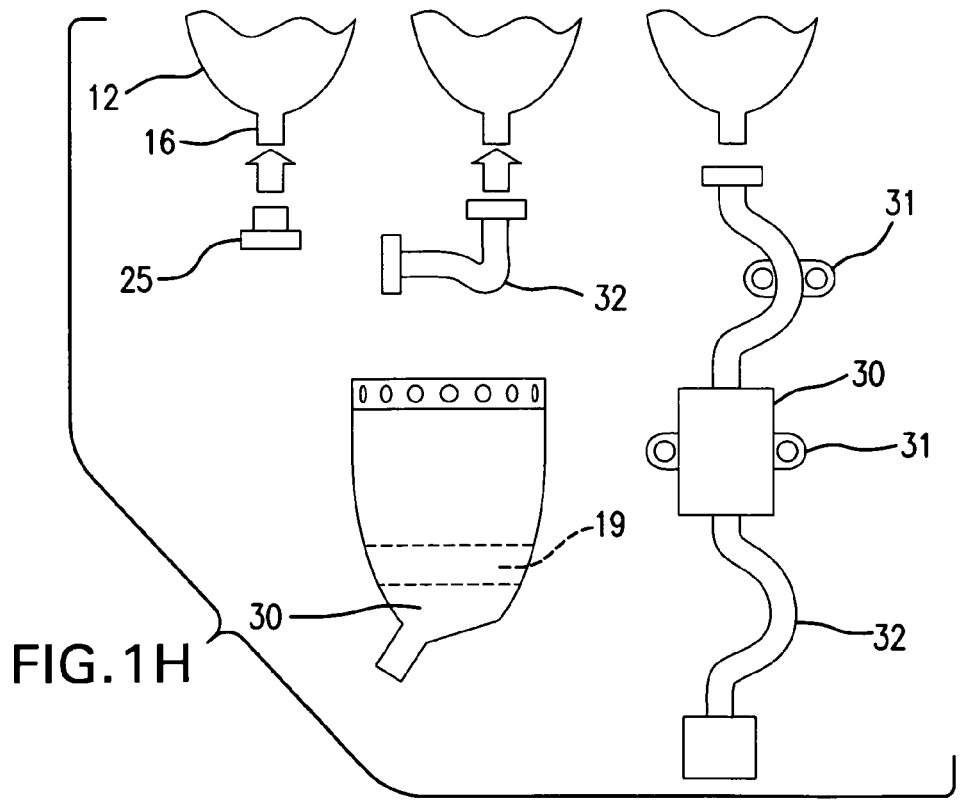

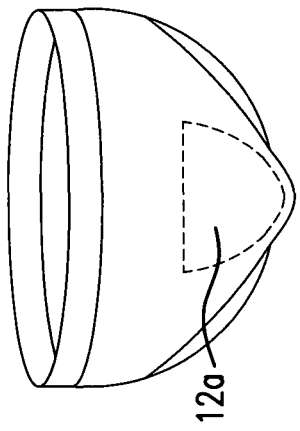
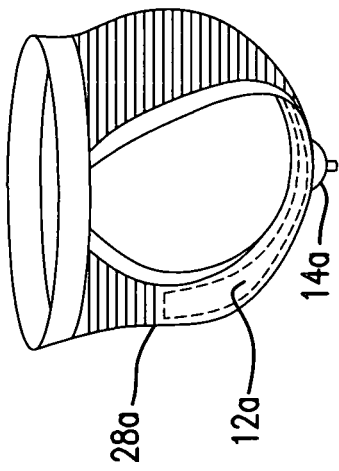
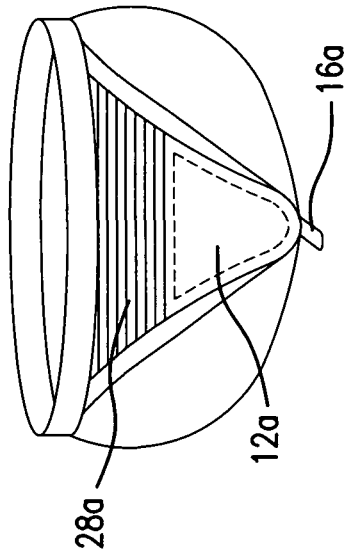
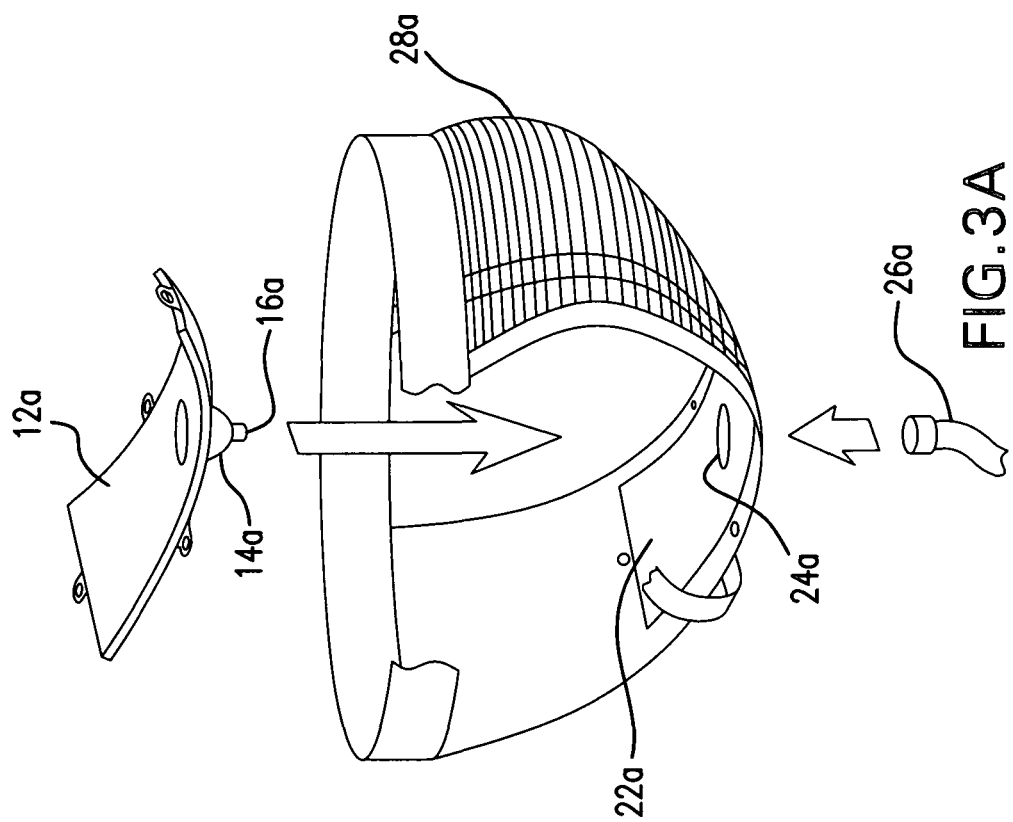

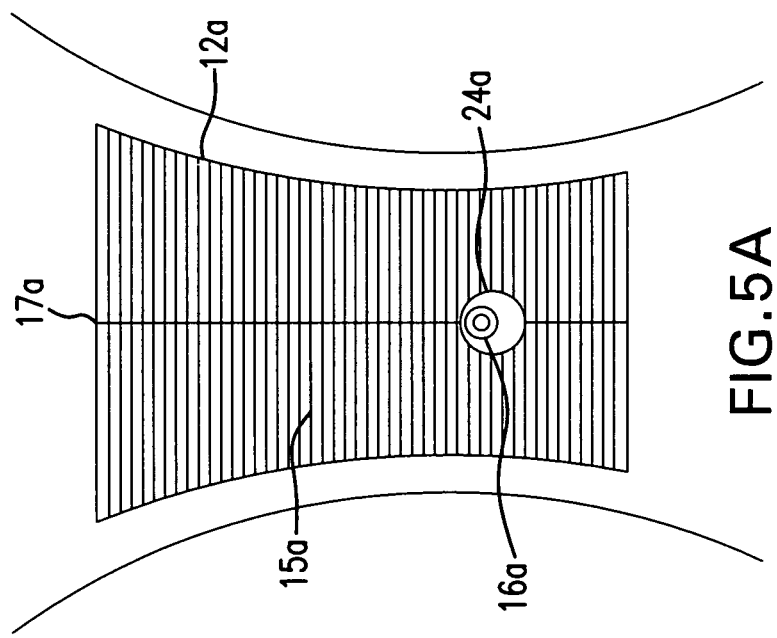
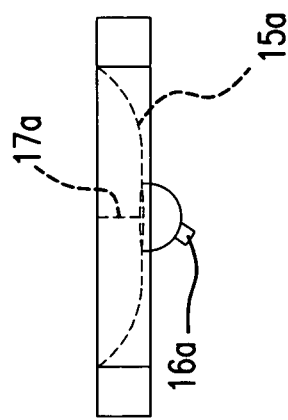
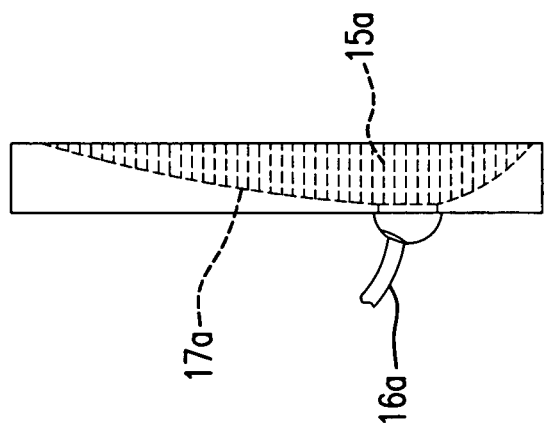
FIG.5A
FIG.5B
FIG.5C

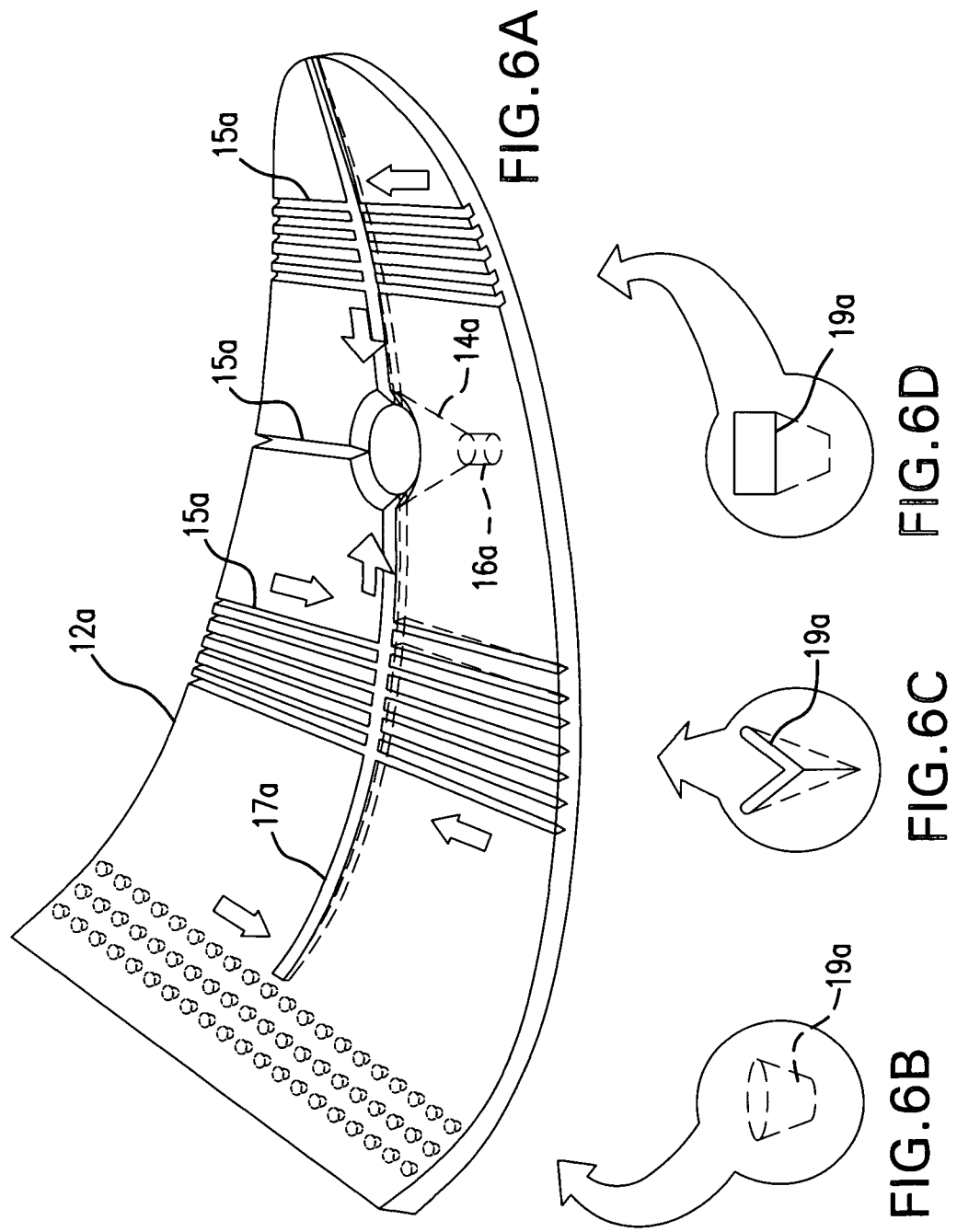

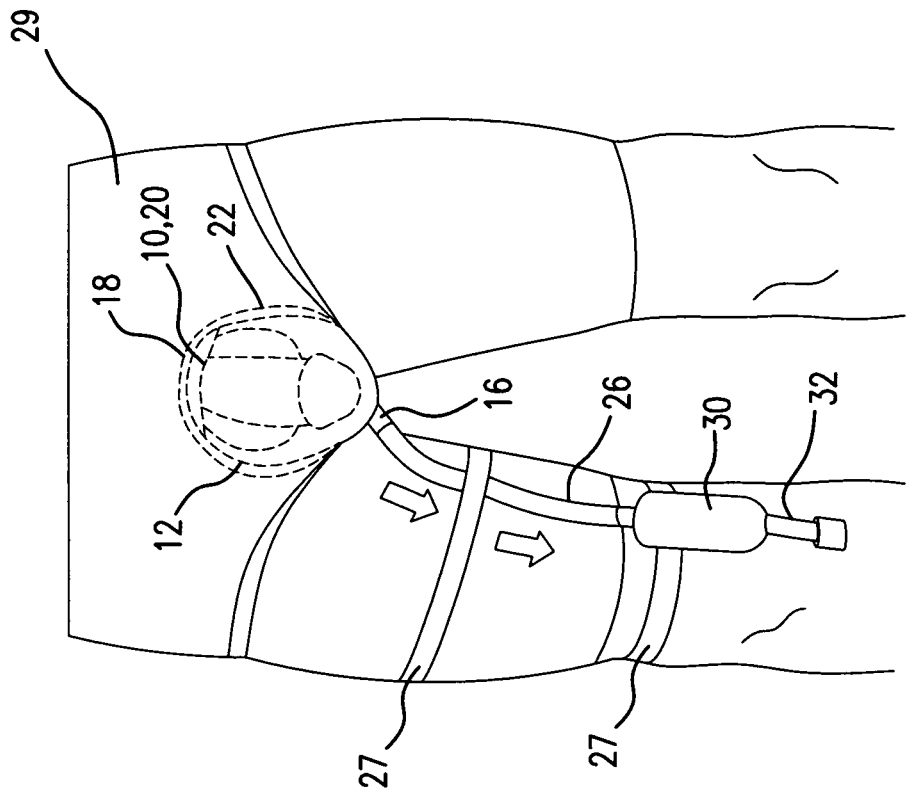
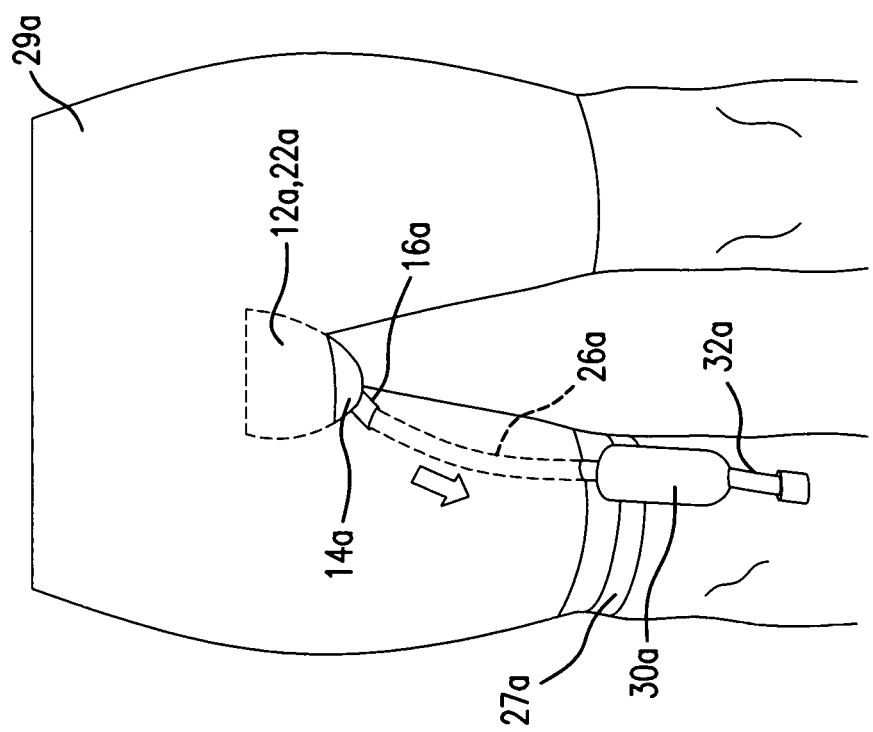

HOLDER

RELATED APPLICATIONS

The present application is a continuation-in-part application of U.S. provisional patent application, Ser. No. 61/125,251, filed Apr. 23, 2008, for HOLDER, by Lester William Medeiros, included by reference herein and for which benefit of the priority date is hereby claimed.

FIELD OF THE INVENTION

The present invention relates to an incontinence device and, more particularly, to an incontinence device that diverts urination from the point of origin to a reservoir to be disposed of.

BACKGROUND OF THE INVENTION

According to the National Institute on Aging, at least one in 10 people 65 or older has urinary incontinence (UI). According to AM News, Mar. 23, 2009, "The problem of urinary incontinence affects millions of people and can happen to anyone, but becomes more common among older people." And, although it is most common among women in this age group, men who have prostate disease also are at increased risk factors involve a number of elements beyond age and sex. They include obesity, smoking, chronic obstructive pulmonary disease and heart failure, dementia, and impaired mobilization. Constipation and urinary tract infections also can cause incontinence". And don't forget prostrate surgery and radiation treatment. These factors translate into millions of people in the U.S. alone with UI problems. Heavy UI can cause social isolation, depression, and even suicide. A new approach the high end UI is needed.

One U.S. Pat. No. 5,926,858 presented a hardware device which was too hard, bulky, and rigid. You can also go to any drug store and find a whole array of pads and underwear that utilize the absorption principal. That is, these devices are very absorptive and will hold onto urine until they are saturated. And if one is not careful, they will wet one's clothing and then the chair or couch one is sitting on. Some times this is sooner than later. An internal catheter involves inserting a tube into one's penis to drain urine from the bladder. In this case, the device was called and external catheter. A condom which is attached to a tubing would be placed over the penis. Then a Valco™ band would wrap around the outside of the condom to secure the condom in place. The tubing would lead into a reservoir that would be strapped to one's leg just like U.S. Pat. No. 5,926,858.

U.S. Pat. No. 5,926,858 seems too hard, rigid and bulky. But using the idea of a drainage hose connecting to a reservoir like the external and internal catheters do is a sound one. This is as long as the leg straps connect to stationary loops and are comfortable. This is not the case for U.S. Pat. No. 5,926,858, internal or external catheters. External and internal catheters use rubber straps that are not bounded to the drainage hose. These slide down and thus are unstable, not to mention the rash they give the user. Absorption pads work somewhat well if one has a very mild incontinence. But if one's incontinence is heavier, beware of forgetting about it for a little while. Because when one feels a little wet, one may have to run to whatever restroom is hopefully near by. Your underwear will get wet very soon after that if nothing is done. Then your pants and maybe the chair or couch you are sitting on is the next victim. So one would have to be alert and have at least one spare in his (her) pocket or purse or maybe in the trunk of one's car. The same holds true for the incontinence underwear. But they hold more urine than the pads do, even though more bulky to carry around. And if one is going to change his (her) incontinence underwear and is wearing pants or slacks, then these have to come completely off before a new one can be put on. And then where does one dispose of the incontinence underwear or pad? It would be nice to have access to a plastic bag to put it into when visiting a friend's house. Or one may want to sneak it out or have an excuse to put it in his (her) car truck so no one will know he (she) is incontinent.

It would be advantageous to provide a solution to urine incontinence whereas the users would have a comfortable and efficient way to dispose of their urine without getting their garments wet. Thus knowing accurately when to drain urine for disposal would come into play. A user could feel how full the reservoir is from the outside of his garments.

It would also be advantageous to provide a way of disposing of urine without having to throw something away like absorption pads away. Imagine yourself at a gathering where you have could have had the choice of either draining urine accumulation in the toilet. Would you want to use this invention or somehow find a sanitation way of disposing a urine absorbing pad.

It would be convenient to provide a way of using the same device without changing anything all day long. And this would be cost effective

SUMMARY OF THE INVENTION

People with bladder issues and those that have had their prostrate surgically removed because of prostrate cancer are but a couple of examples where bad to severe incontinence can be a real issue. This invention especially targets these people. A supporting structure in the form of a modified jock strap or biker's shorts can provide comfort and support. For males with normal size genitalia, a comfortable bag like container is attached to or is part of the supporting structure. This is used for collecting urine at its source for drainage. For females and males with very small genitalia, a unisex pad with a small bag is used for the same reason. The drainage problem is addressed by providing tubing and a storage reservoir whereas urine can be released easily at the convenience of the user. If the incontinence problem is not too severe or the individual has ready access to a rest room, a storage chamber could be right on the bag itself. Other wise a reservoir can be fastened to the side of the user's leg.

The male model may do alright with gravity alone. This is true even when one is resting on his side. A waterproofed bag can be made sufficiently long enough to hang downward whereas the urine flow would rely on gravity to direct the flow to the reservoir for drainage.

But wicking and a trigger device play a large part in the unisex model. Micro channels that having progressively stronger wicking power along a continuum direct flow toward the middle of the pad. A middle channel(s) then directs flow to the lowest point where a small bag is used for collection. But this small bag is made of highly porous hydrophilic material that allows flow to drain downward for disposal. But because it is highly porous, the urine does not wet backwards. It instead drips due to gravity and because of this acts like a pulling mechanism much the same way that transpiration in tree leaves hundreds of feet up pulls up water.

BRIEF DESCRIPTION OF THE DRAWINGS

A complete understanding of the invention may be obtained by reference to the accompanying drawings, when considered in conjunction with the subsequent, detailed description, in which:

FIG. 1E is a side view of an alternative jock strap apparatus;
FIG. 1F is a side view of an alternative jock strap apparatus;
FIG. 1G is a front view of an alternative jock strap apparatus;
FIG. 1H is a group view of a set of miscellaneous components;
FIG. 3A is a plan view of a unisex jock strap apparatus;
FIG. 3B is a front view of a unisex jock strap apparatus;
FIG. 3C is a side view of a unisex jock strap apparatus;
FIG. 3D is a back view of a unisex jock strap apparatus;
FIG. 5A is a top partial perspective view of a unisex pad fitted on the fitted on the crotch area of a unisex jock strap apparatus;
FIG. 5B is a back/front partial perspective view of a unisex pad fitted on the fitted on the crotch area of a unisex jock strap apparatus;
FIG. 5C is a side perspective view of a unisex pad fitted on the fitted on the crotch area of a unisex jock strap apparatus;
FIG. 6A is a top view of a unisex pad;
FIG. 6B is a cross sectional view of a cone shaped micro pore;
FIG. 6C is a cross sectional view of an alternative channel;
FIG. 6D is a cross sectional view of an alternative channel;
FIG. 7A is a front plan view of a unisex bikers pants apparatus;
and
FIG. 7B is a front plan view of a bikers shorts apparatus.

For purposes of clarity and brevity, like elements and components will bear the same designations and numbering throughout the Figures.

DESCRIPTION OF THE PREFERRED EMBODIMENT

Figure 1A:
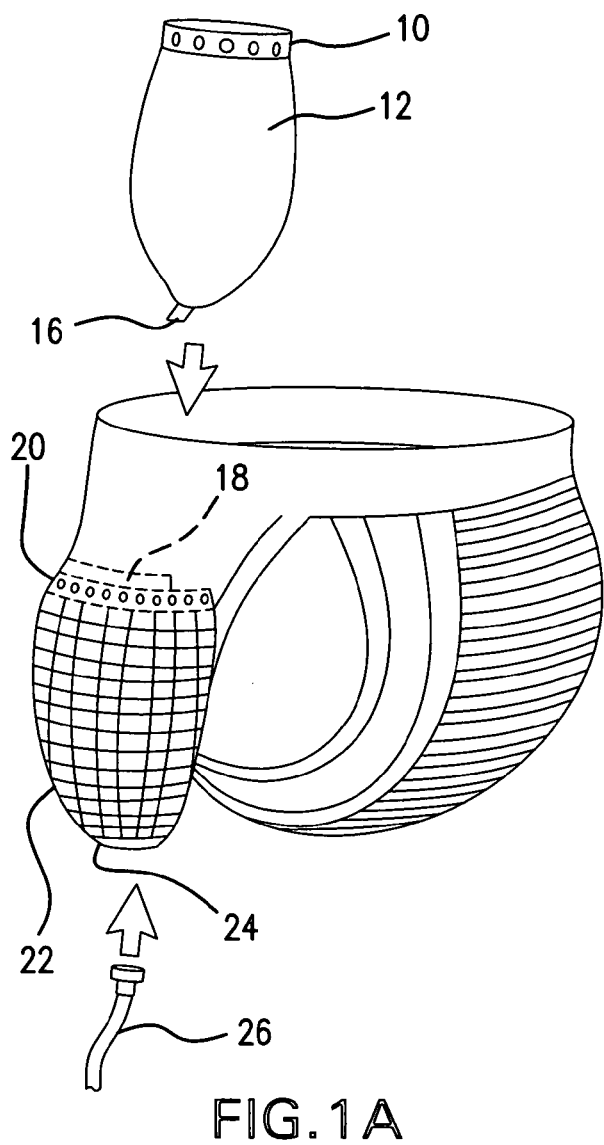
FIG. 1A is a plan view of a jock strap apparatus.

FIG. 1A is a plan view of a jock strap apparatus 28. It shows all the basic components of the invention. The first major component is the bag 12 which is inserted into the holder 22, another major component. The area on the top circumference 10 of the disposable bag 12 attaches or fastens to the corresponding connection area 20 in the holder 22. This area is just below the adjustable elastic band 18. The adjustable elastic band 18 is to secure the male genitals in place at its base. There are literally dozens of ways to do this. These include zippers, buttons, snaps, eyelets, grommets, Velcro, and snap tape. The main idea is to secure these two areas firmly together. But if one has large genitals, the strap may not need to be used.

Figure 1B:
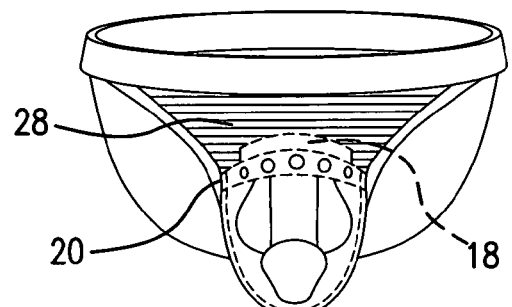
FIG. 1B is a front view of a jock strap apparatus.

Once the bag 12 has been fully inserted and secured, the fitting 16 then protrudes outside of the bag holder 22. This is through an opening at its bottom, the holder hole 24. There the hose 26 is connected to further facilitate urine flow. But a secondary purpose of this connection is to serve as an anchor and stabilizer of the inserted bag 12. FIGS. 1B, 1e, and 1D show the front, side, and back views of the jock strap apparatus 28. The jock strap apparatus 28 itself is the last major component.

FIG. 1B is a front view of a jock strap apparatus 28. It shows the male genitals completely enclosed within the bag 12. Again, the bag 12 is attached by its top circumference 10 to the connection area 20 inside the bag holder 22. The male genitals are secured there by the adjustable band 18. Does it have to be exactly like this? No! It is possible to integrate the adjustable elastic band 18 and the connection area 20 into a single unit at a single location at 18 that provides both functions of connector 21 and male genital securer. Notice that the fitting 16 angles to the left. This aims the attached hose to the inside of the user's leg. This aids in urine flow toward the inside of the user's leg so that the connecting hose 26 can comfortable fit there without any portion of the hose dangling in the front.

FIG. 7B shows the rest of logistics from fitting 16 to hose and plug 32.

Figure 1C:
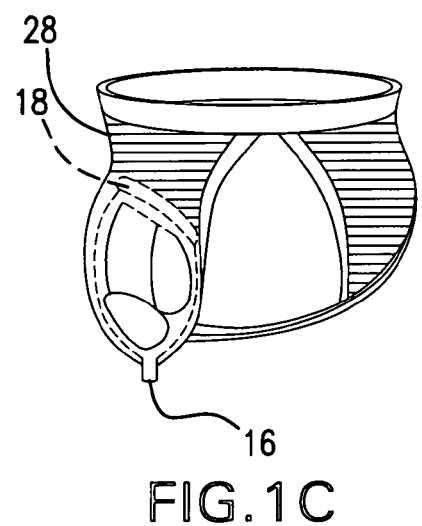
FIG. 1C is a side view of a jock strap apparatus.
Figure 1D:
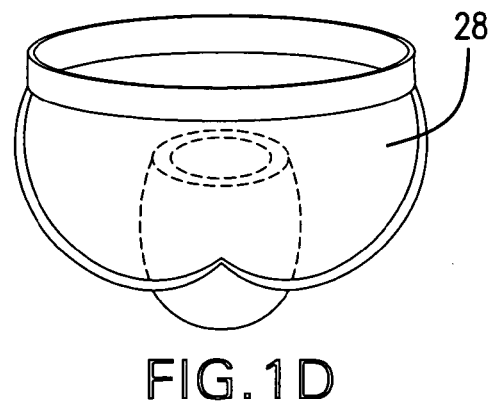
FIG. 1D is a back view of a jock strap apparatus.

FIG. 1C is a side view of jock strap apparatus 28 that has a bag 12 fastened to it with male genitals inserted and secured.

FIG. 1D is a back view of a jock strap apparatus 28. The top ring on the holder 22 is where the male genitals are secured by the adjustable elastic band 18. This back of the jock strap apparatus 28 could be enclosed with a stretchable cloth like those used in bikers' shorts. Bikers' shorts material is comfortable, stretchable, breathable, and enduring.

FIG. 1E is a side view of an alternative jock strap apparatus. This method would have no holder at all. Only the adjustable band 18 together with connection area 20 would hang from in front of the jock strap apparatus 28. A bag 12 would then fasten or connect directly from its top circumference 10 to the connection area 20 on the jock strap apparatus 28. The jock straps would merge into a male connector 21 which would then snap into the counterpart female connector 21 on the bag 12. An advantage of this method is no air flow impediment from the bag holder 22. The bag 12 is left exposed for air to pass through and vapor to pass out from. Also, the system is a less bulky because of this. A disadvantage may be that an integral holder 22 may provide more stability.

FIG. 1F is a side view of an alternative jock strap apparatus. No bag 12 or holder 22 is use here at all. Instead of a bag 12 or a bag holder 22, a permanent integral pouch 23 would be a part of the jock strap urination incontinence device. It would function similar to the bag 12. Let us go back to FIG. 1A. There would be no bag 12 to insert into the holder 22. And Instead of holder 22, there would be a pouch 23. The male genitals would insert directly in there. The adjustable band 18 would be a part of the pouch 23. No connection area 20 however would be needed. A disadvantage of this method would be the cleaning and sanitation of the pouch 23 which is an integral part of the jock strap apparatus 28.

FIG. 1G is a front view of an alternative jock strap apparatus. This method would have the setup the same as FIG. 1A except that the bag 10 and the holder 22 are elongated more. This would allow the reservoir 30 to be directly connected to the bag in lieu of it being connected onto a leg as in FIG. 7B. A stopper 25 could drain urine directly from the disposable bag 12. Or the hose and plug 32 shown in FIGS. 1H and 7B could be used in lieu of the stopper 25. A variation of this method would be to have a permanent pouch 23 like in FIG. IF. Only that the pouch 23 would be elongated and have a reservoir 30. A definite advantage of these two methods is to eliminate the contraption from the fitting 16 all the way down to the hose and plug 32 as in FIG. 7B.

FIG. 1H is a group view set of miscellaneous components. This is like a components store. These components are applicable to the jock strap apparatus 28, as was done above. It is also applicable to the unisex jock strap apparatus 28a and all their alternatives. The picture of the top left is especially suited for and shown in FIG. IG. The top middle picture is an derivative of the top left picture. It has the added feature of a short lengthen hose used for drainage. This gives a little longer reach. The top right picture basically shows the contraption used in FIGS. 7B (and 7A) with the added feature of loops where straps 27, FIG. 7B can insert into. These help stabilize the straps 27 from sliding down the leg of a user. Straps should have comfortable linings in the side contacting the leg. The slope on the bottom of the shown bag is applicable to both the unisex bags 14*a*, FIG. 3A and the bags 12 for males. This aids in urine flow toward the inside of the user's leg so that the connecting hose 26 can comfortable fit there without any portion of the hose dangling in the front.

As alluded to in FIG. 1A, the holder 22 provides a space for the bag 12 to be put into and anchored. There should be great confidence in the bond of the attachment between the bag 12 and holder 22. One done, this lends itself ideally for the holder 22 being fabricated with large open spaces with strong slender fibers. In other words, one will not need the holder 22 to act as a backup. The holder wouldn't need to be composed of the same materials and structure as the bag 12. Of course, this would be another alternative. FIG. 1A illustrates this with a grid like bag holder 22. Therefore air can reach the disposable bag's 12 pores more readily and vapors inside the disposable bag can be more quickly released because of its open air ness.

The composition of the bag 12 is very important. The optimum of design would be waterproofed with a membrane from the inside. Also should be breathable, comfortable, a deodorizer, that controls fungi, dries quickly, chemical resistance, and is relatively inexpensive. As a matter of fact, a permanent replaceable, washable bag 12 could be used instead of a disposable bag 12.

Trap Tek is one of the companies that manufactures a fabric that meets these criteria:

Eco-friendly is a key theme.

Cocona fabrics and yarns from Trap Tek in the US are made from coconut shells and provide evaporative cooling by pulling moisture away from the skin and spreading it across the fabric surface.

Activated carbon embedded within the yarns and fibres also absorbs harmful UV rays, and depending on fabric construction and Cocona content, up to 30 Ultraviolet Protection Factor (UPF) can be provided. Odour molecules, too, are trapped by the activated carbon, and are then released and the carbon refreshed by the heat from washing and drying.

Coconut activated carbon is a recycled, sustainable material, since coconut shells are a waste product from the food industry. Cocona yarns may be blended with cotton and wool as well as man-made fibres.

Barriers and Antimicrobials:

Waterproof, windproof and breathable Skyair membranes from the UK company Skymark are developed around the latest resin and manufacturing technology, and are recommended for both outdoor clothing and the health care field.

Skyair is a monolithic membrane and free from any pores; which means that it is an excellent bacterial barrier whilst also being breathable. In hospital environments and operating rooms it can protect staff from bacteria, viruses, blood and other fluids, while still being comfortable to wear.

Aegis Enhanced is a comprehensive range of antimicrobial chemical treatments developed by the Belgian Devan Group, which provide additional functionalities to enhance comfort and well being.

These include a host of different chemical finishes for moisture management, stretch recovery, sensory management, shrink resist, flame retardant, and anti static technology—all of which are also antimicrobial.

Omniflex, Inc. of Greenfield, Mass. has the superior membrane that can be laminated onto fabric to produce similar results as Trap Tex. Most of their products have a thin, waterproof-breathable textile composite that maximizes comfort, is puncture and chemical resistance. Instead of multiple layers because it is a monolithic composite, that is cost effective and lends itself to disposables.

Cannondale manufactures a product call Termal Carbon Hydrogrid Max. Now for increased moisture wicking and odor adsorption, the website http://www.waterproofworld.co.uk/fabrics.htm has a list of fabrics that meet these criteria except maybe the deodorization function. For example:

Kiba-Flex™ is Kiba's own breathable fabric is 100% wind and waterproof material and breathable. It is soft and flexible and gives a large freedom of movement, is light and comfortable to wear, provides a high level of comfort and is slightly oil and chemical resistant.

Others fabrics made by waterproofworld that meet the above criteria include Togz Fabric, Regatta Hydrafort, Regatta Isotex 5000, Regatta Isolite 5000 is 100% breathable and waterproofed, and others. Some of these are 100% breathable and all are machine washable.

But if deodorizing is ever a problem, this could be overcome by Nature's Miracle Litter Treatment. Natural enzymes make it work. Nature's Miracle Litter Treatment uses natures enzymes in dry form to eliminate urine odors. These enzymes are activated upon contact with the urine. Plus, the ingredients in Nature's Miracle Litter Treatment produce new enzymes which continue to neutralize the new urine odor each time the animal (human) urinates.

Figure 2:
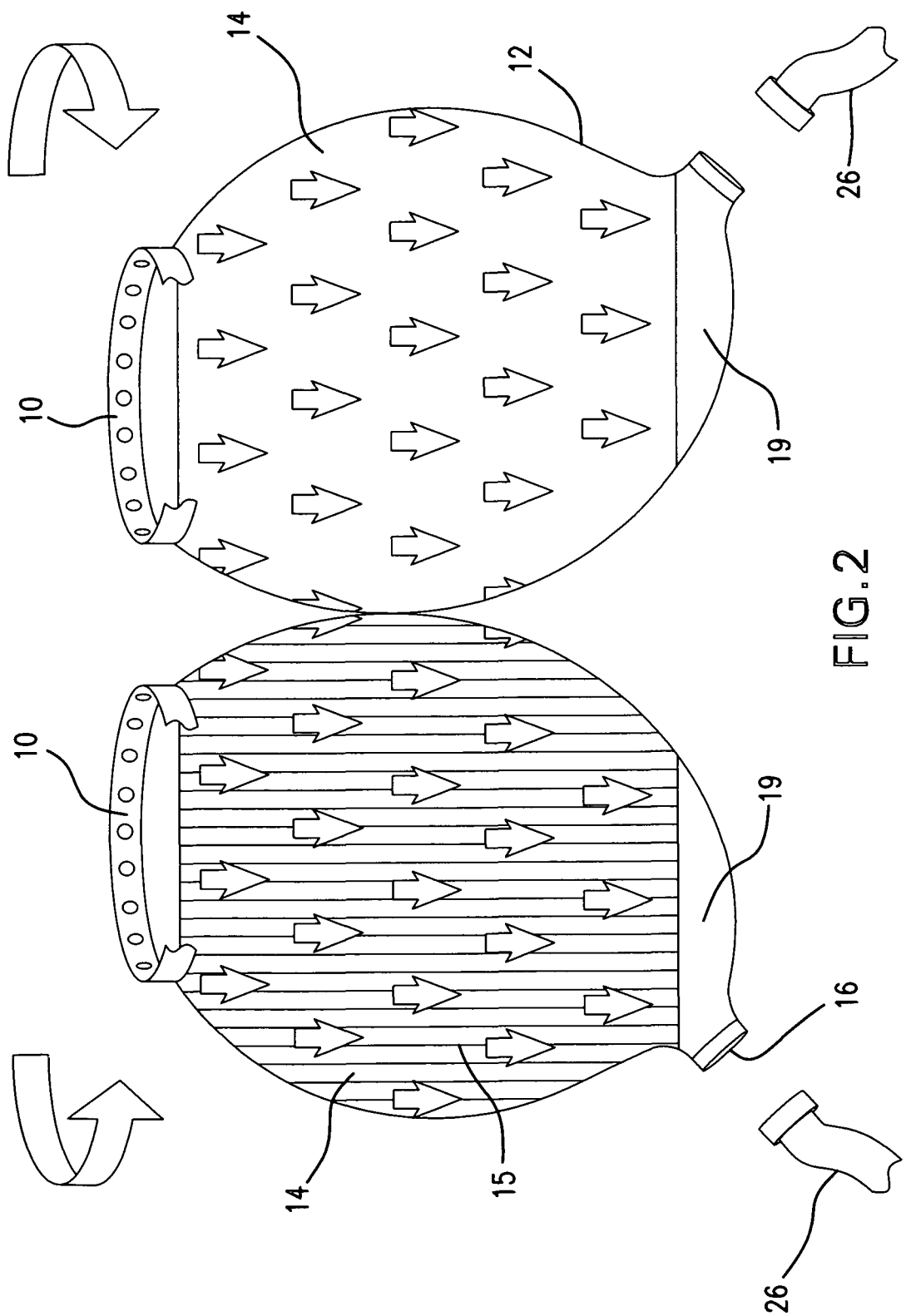
FIG. 2 is an open bag view view of an alternative showing two possibilities.

FIG. 2 is an open bag/pouch 23 view of an alternative showing two different possibilities. As discussed above, the bag itself should be waterproofed from the inside, breathable, comfortable, quick drying and relatively inexpensive. The arrows in each illustration indicate that urine origination flows downward, especially if the individual wearing this contraption is in an upright position where gravity is a contributing factor. The left half shows vertical micro channels 15 spaced out evenly throughout the bag. These further facilitate the flow to the trigger zone 19 by wicking. The urine is wicked along the troughs of vertical micro channels 15 until each that is exposed is equally wet. But vertical micro channels made of long parallel fibers that are tapered from top to bottom have a strong downward tendency to wick moisture in each channel gets narrower and narrower the hydrophilicity gets stronger and stronger. This forms a continuum of stronger and stronger hydrophilicity. This is discussed in 6C below. When the urine reaches the trigger zone 19, something different happens. The trigger zone 19 should have even a greater pull of urine than the vertical micro channels. This is because the zone should be made of a highly porous hydrophilic material such as cellulose. But since such material is highly permeable, the urine cannot rise back up to equalize the wetness throughout the system. Thus it drips out to the hose. The drip acts similar to the transpiration pull from leaves of trees that carry water hundreds of feet up from their roots. One purpose of this process is to eliminate pockets of droplets clinging to the inner walls of the male disposable bag. Another is to facilitate flow for discharge even when one is resting in a horizontal position. A bag made a little longer would have the gravitational hang factor to contribute to this. Still, it is it possible to achieve these results by chemically coating the inside of the bag with a stronger and stronger wicking substance from top to bottom? If the coating doesn't interfere too much with the ability for the bag 12 or pouch 23 to breathe or be waterproof, then yes. So the bag 12 would have to be made of material that is chemical resistance. But this solution would probably be best for the disposable bag only and not for the pouch 23 acting as a permanent resident such as a pouch 23. This is because the coating wears off after a while and would have to, be replenished-a less costly but inferior method.

The right half shows another inside bag alternative. Here there are no channels. There are a number of options here. The inside could be merely made of film that is waterproofed, breathable, a deodorizer, comfortable, quick drying and relatively inexpensive up to the trigger zone 19. This would be less costly than the left half of FIG. 2. Here urine just races down the sides of the male disposable bag to the trigger zone 19 when one is in an upright position. In a lying down position at night, the disposable bag could be adequately long enough whereas it hangs downward. Then the flow goes through the hose 26 onward to final drainage. The reservoir 30 in FIG. 7B could then hook onto some kind of stand. Or as mentioned for FIG. 1G above, the reservoir 30 could be on the bag 12 itself.

Then another alternative would be exactly as described in the preceding paragraph except for no trigger zone 19. This would make the cost even cheaper yet with maybe no undesirable loss in drainage ability.

FIG. 3A is a plan view of a unisex jock strap apparatus 28a. It is an alternative to the jock strap apparatus 28 above and as the name implies can be used by both male and females. This may be the option for a male with very small genitals as the methods above may not work here. Like FIG. 1A, FIG. 3A shows all the basic components of the invention. The first major component is the unisex disposable pad 12a. It is fastened unto the unisex pad holder area 24a. One way as shown, is by applying the four (4) snaps on the unisex disposable pad 12a unto the corresponding counterpart on the unisex pad holder 22a. Once done, the whole unisex bag 14a on the unisex pad should protrude out of the pad holder hole 24. The unisex hose 26a can then be fastened unto the unisex fitting 16a.

FIG. 3B is a front view of a unisex jock strap apparatus 28a. Notice that the unisex fitting 16a aims to the left. This aims the attached unisex hose 26a to the inside of the user's leg. FIG. 7A shows the rest of logistics from the unisex hose 26a to the unisex hose and plug 32a.

FIG. 3c is a side view of a unisex jock strap urination incontinence device.

FIG. 3d is a back view of a unisex jock strap urination incontinence device.

Figure 4:
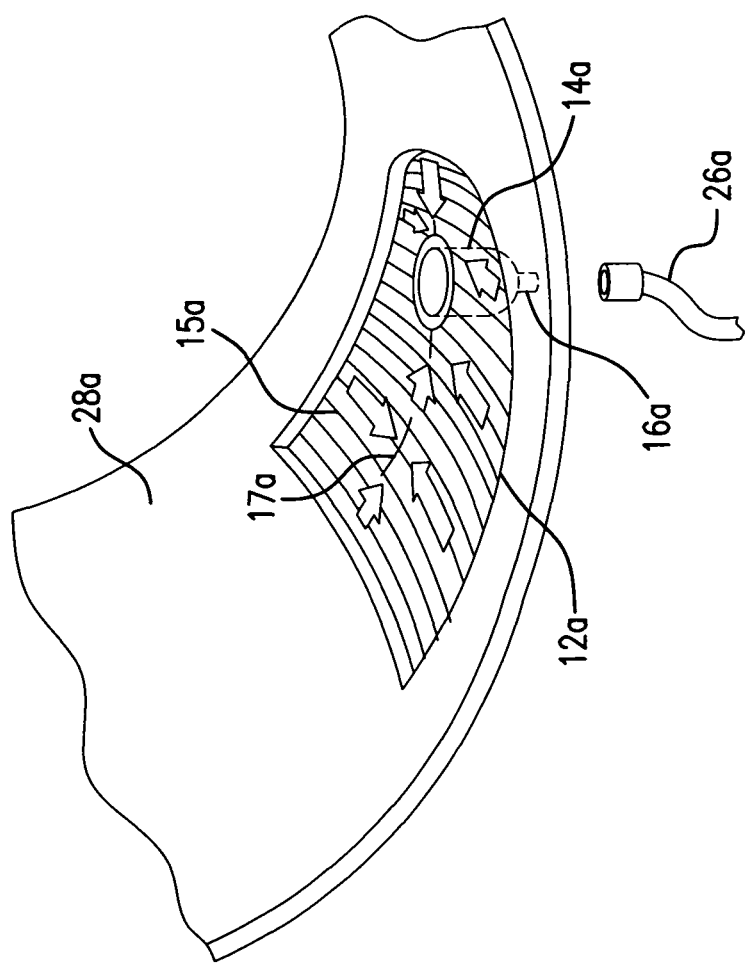
FIG. 4 is a top partial view of a unisex disposable pad fitted on the crotch area of a unisex jock strap apparatus.

FIG. 4 is a top partial view of a unisex disposable pad 12a fitted on the crotch area of a unisex jock strap apparatus 28a, FIG. 3A. Lateral micro channels 15a that are embedded in the pad 12a wick or other wise carry urine from its source to a central micro channel 17a, that is also embedded in the pad 12a. Those perpendicular to the bag wick directly to the unisex disposable bag 14a itself. It should be noted here, that the central channel 17a could in fact be parallel central channels bound together to produce a stronger wicking affect. In fact, I will use the term central micro channel 17a to refer to two (2) parallel channels adjacent to each other. Therefore, lateral channels 15a on one side will connect to the central micro channel on that side. Lateral channels 15a on the other side will connect to the other central micro channel 17a on that other side. The arrows show the direction of flow from the lateral channels 15a to the central channel 17a to the unisex bag 14a. From there the flow is to the unisex bag 14a and then out to the unisex hose 26a. A more thorough explanation on the mechanics involved will be explained in FIGS. 5A to 6D below. The description of FIGS. 5A to 5C below would best be served by viewing the corresponding reference numbers on FIG. 6A at the same time.

It should be noted here that the composition of the material that the channels are embedded in should be of the quality found in a film made by companies such as Skyair or Omniflex, Inc. This insures that the film will be thin, tough, waterproofed, breathable, and chemical (urine) resistance. Underlying fabric by could be made by Trap Tex. This insures material that would provide a waterproofed, deodorizing, breathable, and comfortable. See the commentary at the end of the FIG. 1H

FIG. 5A is a top partial perspective view of a unisex disposable pad 12a fitted on the crotch area of a unisex jock strap apparatus 28a as also shown in FIG. 4. Lateral micro channels 15a straddle and feed into the central channel 17a, which in turn feeds into the unisex disposable bag 14a via the pad holder hole 24. The lateral channel 15a that is perpendicular to the unisex bag 14a flow directly to it. These channels form corridors or compartments. Urine flows from their opened spaced rectangular tops that are flush with the top of the unisex disposable pad 12a. Then it flows along their two inner sides, sometimes under hydraulic pressure if these corridors fill up. If so, this may create a vacuum that in turn creates a sucking "pull". From there it flows to their slopping bottoms. The slopes of the bottoms of either the lateral micro channels 15a or of the central channel(s) may be either curvature, straight or in any other manner.

FIG 5B is a back/front partial perspective view of a unisex disposable pad fitted on the crotch area of a unisex jock strap apparatus 28a. For illustration purposes, only one lateral channel's bottom is shown in FIG. 5B, that being one of those lowest ones that are perpendicular to the pad hole 24. To draw a lot of lateral channels intersecting the pad holder hole 24 or the central channel 17a would prove to be way far too unwieldy. As you can see, the lateral micro channel's 15a bottom slopes downward to the central channel's (17a) bottom. The top of these channels like all the others remain flush with the top of the unisex disposable pad. The central channel's bottom in turn slopes downward from both ends and reaches its lowest point at the pad holder hole 24.

FIG. 5C is a side partial perspective view of a unisex disposable pad fitted on the crotch area of a unisex urination incontinence device 28a. Here we can draw pairs of lateral channels 15a that straddle the central channel 17a. These are shown as single dashed single lines (although in actuality if we magnified them, they would also have measurable width). This is because each pair of lateral channels 15a is in the same plane from both sides of the central channel 17a. A lateral channel's 15a bottom would start at the far side top, slope down to intersect the central channel's 17a bottom. Then from the bottom, the corresponding lateral channel 15a on the other side of the central channel 17a would slope back upward to intersect the near side top. You would note that the slope of the lateral channels and central channel are exaggerated for illustration purposes. The standard drainage slope is ¼", per foot or about a rise to run of 0.021.

I will give an illustration. It will be understood that when I mention slope, I will be talking about the slope at the bottom of the micro channels. I will start with the central micro channel 17a. I will use the standard drainage slope of ¼ inch per foot and a straight line slope. I will also use a run of 4 inches from the far side. The lowest drop would be at the pad holder holea where it drains into the unisex disposable bag 14a. This drop would be ⅓ of ¼ inch=$\frac{1}{12}$ inch since the 4 inches run is ⅓ of 12 inches. The central channel's 17a slope would be a constant m=$\frac{1}{48}$ or (¼ inch divided by 12 inches) throughout. Now what if the lateral channels 15a all have a runs of say 2 inches on each side of the central channel 17a. The deepest end would still be same $\frac{1}{12}$ inches. But in this case, a lateral micro channel 15a that runs into the deepest end would have a slope of $\frac{1}{12}$ inches divided by 2 inches=$\frac{1}{24}$, or double that of the central channel's constant m=$\frac{1}{48}$. Of course as we move further towards the two ends of the central channel away from the pad holder holea, the lateral channels connecting to the central channel would have slopes approaching zero. Therefore in this illustration, the lateral slopes would range from close to zero at the ends of the central channel to m=1/24 at the pad holder holea. The central micro channel's 17a slope would be a constant 1/4s. And the depths of both the central channel 17a and lateral channels 15a would run simultaneously from near 0 to 1/12.

An option would be to modify the central channel 17a only. It would still be situated on the pad 12a as shown in FIG. 5A. But instead of running from the top of the unisex pad 12a downward as shown in FIG. 6A, the top of the central channel 17a would lie beneath the surface where its bottom once was. The lateral channels would be situated exactly as before. So the bottoms of the lateral channels 15a would meet the top of the central channel 17a at their lowest point at the center of the pad. That is, the lateral channels 15a would start from one end, "run over" the central channel 17a, and end up on the other side-one continuous line. As before, the central channel 17a would run into the pad holder holea which would now be relatively lower.

In this scenario, the central channel could be a strand of very narrow channels bound together. These would make wicking of the central channel 17a stronger than before. Thus, it would have more of a pulling affect on the urine in the lateral channels 15a.

FIG. 6A is a top view of a unisex incontinence pad. This drawing is a three dimensional composite of the unisex disposable pad 12a portion of 5A, 5B and 5C. The objective of all the micro channels is to use gravity and wicking to direct urine from its source on the unisex pad 12a to the unisex bag 14a. Unlike the trigger zone 19 in each half of FIG. 2, the entire inside of the unisex bag 14a is a trigger zone 19. The trigger zone 19 has even a greater pull of urine than the lateral micro channels 15a or the central micro channel 17a. Again, this is because the zone should be made of a highly hydrophilic material such as cellulose. But since such material is highly permeable, the urine cannot rise back up to equalize the wetness throughout the system. Thus it drips out to the hose. The drip acts like the transpiration pull from leaves of trees that carry water hundreds of feet up from their roots.

Options that can be applied to the unisex bag 14a and the unisex fitting 16a can be found in FIG. 1G. An elongated bag 14a with its built in reservoir with as shown on the top of FIG. 1G may prove useful here. This could be used in lieu of the unisex bag 14a and eliminate altogether the contraption shown on the far right of FIG. 1H and also shown in FIG. 7A from 16a down to 32a. A stopper 25 would drain urine directly from the unisex bag 14a. Or the hose and plug 32a shown in FIG. 1H and FIG. 7A could be used in lieu of the stopper 25. The hose would be of a short convenient length.

The unisex pad 15a could be of the type that is permanently embedded into the crotch area of the unisex jock strap apparatus 28a or of a disposable variety.

FIG. 6B is a cross sectional view of a cone shaped micro pore. The cone shape ensures that wicking will become progressively stronger from top to bottom. These are embedded in a film made by companies such as Skymark and Omniflex, Inc. to insure a waterproofed film throughout that is breathable, comfortable, and chemically resistant. And the underside could be made of fabrics by a company such as Trap Tek that control odors and bacteria. These materials were discussed above. These same fabrics and films can be used in the discussions of FIG. 6B here and for 6C and 6D below.

What happens here is the pores make contact with a sub floor that is thin and highly hydrophilic. This spreads the urine thin until it either dries quickly or is pulled in by the even higher hydrophilic porous trigger zone 19 material in the unisex bag. Another variation of this would be to have the sub floor to have a continuum of higher and higher hydrophilicity until it reaches the trigger zone 19 material in the unisex bag 14a.

FIG. 6C is a cross sectional view of an alternative micro channel. The solid v shaped figure shows the lateral micro channel 15a at its start on the edge of the unisex pad 12a. Having both lateral micro channels 15a and the central micro channel have "v" shapes from the top to the bottoms conduce urine flow downward. This is in additional to gravity. But there is more. The height of the "v" gets progressively larger and larger while the inner angle gets progressively smaller and smaller. When the lateral micro channel 15a reaches the central micro channel 17a, the lateral channel's height is at its maximum while the inner angle is at its minimum. The dashed lines show this. As the inner angle progressively gets smaller and smaller, wicking gets progressively stronger and stronger. Thus urine is pulled toward the central micro channel 17a. As mentioned above, the central micro channel 17a is used here to refer to two (2) parallel adjacent channels. Now the tops of each of these central micro channels will be somewhat smaller in width than the lateral micro channels 15a that connect either of them. Thus the wicking power of the two central micro channels 17a is stronger than the wicking power of the lateral micro channels that connect to them, at each and every dept. That means that the two central micro channels 17a will pull the urine in from the lateral micro channels. To continue, the two (2) central micro channels have the tendency to pull urine to the unisex bag 14a for the same reason that the lateral micro veins 15a pull urine towards the two (2) central micro channels 17a. That is because the inner angles of the "v" are progressively getting smaller toward the deep end where they intersect the unisex bag 14a. So what does this all mean? It means that even though one is lying on his/her side, the lateral micro channels will pull urine upward toward the central micro channels 17a. Then the flow proceeds to the unisex bag 14a.

FIG. 6D is a cross sectional view of an alternative channel. If the two vertical sides slope inward somewhat, the analysis would be similar to 6C. But there would be more space and volume capacity at the bottom to carry a larger volume of urine. But wicking strength would be compromised somewhat. Thus the pull of the trigger zone 19 in the unisex bag would need to be more important. This method is also cheaper to employ.

FIG. 7A is a front plan view of a unisex biker's pants apparatus 29a. Instead of a jock strap as the supporting vehicle for the unisex jock strap apparatus 28a, we have bikers pants. The material used in the bikers is comfortable, stretchable, induring and can be snugly fit to keep the apparatus stable.

FIG. 7B is a front plan view biker's shorts apparatus 29. Instead of a jock strap as the supporting vehicle of the male jock strap apparatus, we have bikers' shorts.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An apparatus for keeping a male user's underwear and lower garment free of urine from urinary incontinence, comprising:

a breathable jock strap (28) having a front portion and a back portion, wherein the front portion comprises a first connection area;

a urine-collecting bag (12) comprising:
  (i) a top portion and a bottom portion, wherein the top portion comprises a top opening and the bottom portion comprises a bottom opening, the top opening configured to receive a genitalia of the male user;
  (ii) a plurality of vertical micro channels (15) on an inside of the urine-collecting bag, the plurality of vertical micro channels configured to wick urine toward the bottom portion of the urine-collecting bag;
  (iii) a trigger zone (19) made of porous hydrophilic material located below the plurality of vertical micro channels and above the bottom opening, configured to suck urine from within the urine-collecting bag to outside of the urine-collecting bag; and
  (iv) a second connection area (20) at a circumference of the top opening, the second connection area configured to fasten directly to the first connection area;

an adjustable band (18) configured to secure the genitalia of the male user to the apparatus; and a fitting (16) provided at said bottom opening for transporting urine away from the urine-collecting bag.

2. The apparatus according to claim 1, further comprising a stopper connected directly to the fitting.

3. The apparatus according to claim 1, further comprising a hose and plug combination connected directly to the fitting.

4. The apparatus according to claim 1, wherein the jock strap further includes a bag holder surrounding the urine-collecting bag, wherein the bag holder comprises a hole (24) at a bottom such that the fitting (16) protrudes through to the outside of the bag holder.

5. The apparatus according claim 4, wherein the bag holder is integral to the jock strap.

6. A unisex apparatus for keeping a user's underwear and lower garment free of urine from urinary incontinence, comprising:

a breathable strap apparatus (28*a*) having a front area, a back area, and a crotch area provided with a pad holder hole (24), the crotch area comprising a top surface configured to face the user;

a stretchable breathable unisex pad (12*a*) fastened onto said top surface;

a hydrophilic unisex bag (14*a*) integral to the unisex pad such that a top opening in the unisex bag forms an opening through an entire thickness of the unisex pad, the unisex bag provided with a fitting (16*a*) at a bottom end, wherein the unisex bag protrudes through said pad holder hole to facilitate removal of urine from the user;

a central micro channel (17*a*) embedded in the unisex pad, the central micro channel extends in a front-to-back direction of the unisex pad and intersects the top opening of the unisex bag to facilitate urine flow into the unisex bag; and a plurality of non absorptive lateral micro channels (15*a*) embedded in the unisex pad to facilitate urine flow into the central micro channel.

7. The unisex apparatus of claim 6, further comprising a stopper connected directly to the fitting.

8. The unisex apparatus of claim 6, further comprising a hose and plug combination connected directly to the fitting.

\* \* \* \* \*